US00PP20360P2

(12) United States Plant Patent
van den Dool

(10) Patent No.: US PP20,360 P2
(45) Date of Patent: Sep. 29, 2009

(54) ***TRACHELOSPERMUM* PLANT NAMED 'SUNLOVER'**

(50) Latin Name: *Trachelospermum jasminoides*
Varietal Denomination: Sunlover

(76) Inventor: Peter van den Dool, 6e Tochtweg 1K, 2741 KR Waddinxveen (NL)

( * ) Notice: Subject to any disclaimer, the term of this patent is extended or adjusted under 35 U.S.C. 154(b) by 0 days.

(21) Appl. No.: 12/283,665

(22) Filed: Sep. 15, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Kent L Bell
(74) *Attorney, Agent, or Firm*—Penny J. Aguirre

(57) ABSTRACT

A new cultivar of *Trachelospermum jasminoides*, 'Sunlover', characterized by its gold and green variegated foliage, its upright growth habit with strong stems, and its compact plant habit.

3 Drawing Sheets

Botanical classification: *Trachelospermum jasminoides*.
Variety denomination: 'Sunlover'.

BACKGROUND OF THE INVENTION

The present invention relates to a new and distinct cultivar of *Trachelospermum jasminoides* and will be referred to hereafter by its cultivar name, 'Sunlover'. 'Sunlover' is a new cultivar of star jasmine grown for use as a landscape plant.

The Inventor discovered 'Sunlover' as a naturally occurring branch mutation of *Trachelospermum jasminoides* 'Variegata' (not patented) in a container at his nursery in Boskoop, The Netherlands in June 2000.

Asexual reproduction of the new cultivar was first accomplished by the Inventor using softwood stem cuttings in September 2000 in Boskoop, The Netherlands. The characteristics of *Trachelospermum jasminoides* have been determined to be stable and are reproduced true to type in successive generations.

SUMMARY OF THE INVENTION

The following traits have been repeatedly observed and represent the characteristics of the new cultivar as grown outdoors in trial beds and in containers in Boskoop, The Netherlands. These attributes in combination distinguish 'Sunlover' as a unique cultivar of star jasmine.

1. 'Sunlover' exhibits gold and green variegated foliage.
2. 'Sunlover' exhibits an upright growth habit with strong stems.
3. 'Sunlover' exhibits a compact plant habit.

'Sunlover' differs from its parent plant, *Trachelospermum jasminoides* 'Variegata', in having gold and green variegated foliage whereas 'Variegata' has white and green variegated foliage. 'Sunlover' also differs from 'Variegata' in having stronger and more upright stems and in having a more compact plant habit. There are no other variegated cultivars of *Trachelospermum jasminoides* known to the inventor.

BRIEF DESCRIPTION OF THE DRAWING

The accompanying colored photographs illustrate the overall appearance and distinct characteristics of 2 year-old plants of the new star jasmine as grown outdoors in 19 cm containers in Boskoop, The Netherlands. The photograph in FIG. 1 illustrates the overall appearance of 'Sunlover' in bloom. The photograph in FIG. 2 provides a close-up view of the foliage of 'Sunlover', the photograph in FIG. 3 is a close-up view of the flowers of 'Sunlover', and the photograph in FIG. 4 provides a comparison of 2 year-old plants of 'Sunlover' (left) and 'Variegata' (right) grown under the same conditions. The colors in the photographs are as close as possible with the digital photography techniques utilized and the color values cited in the detailed botanical description most accurately describe the colors of the new star jasmine.

DETAILED BOTANICAL DESCRIPTION

Figure 1:
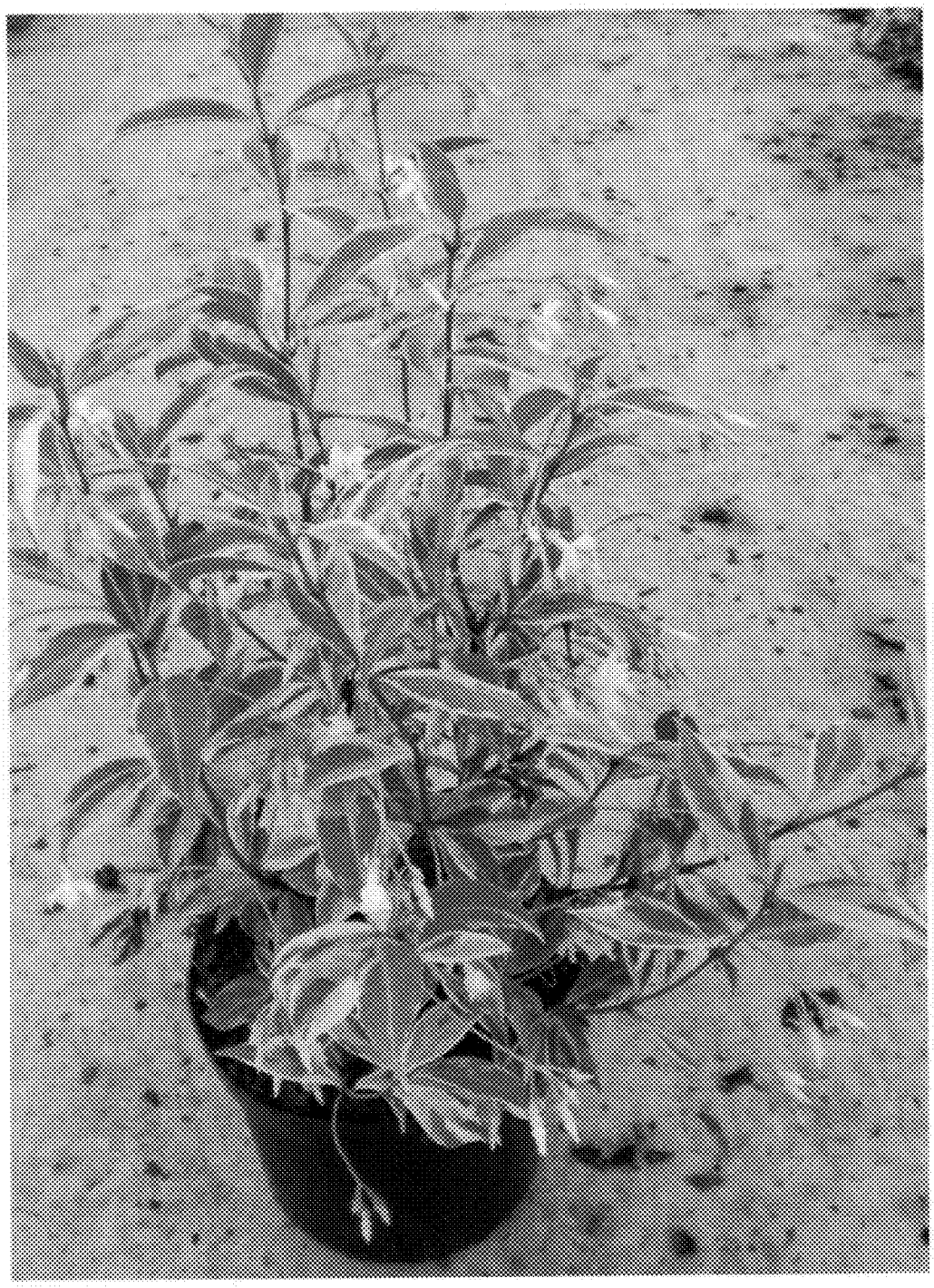
Figure 2:
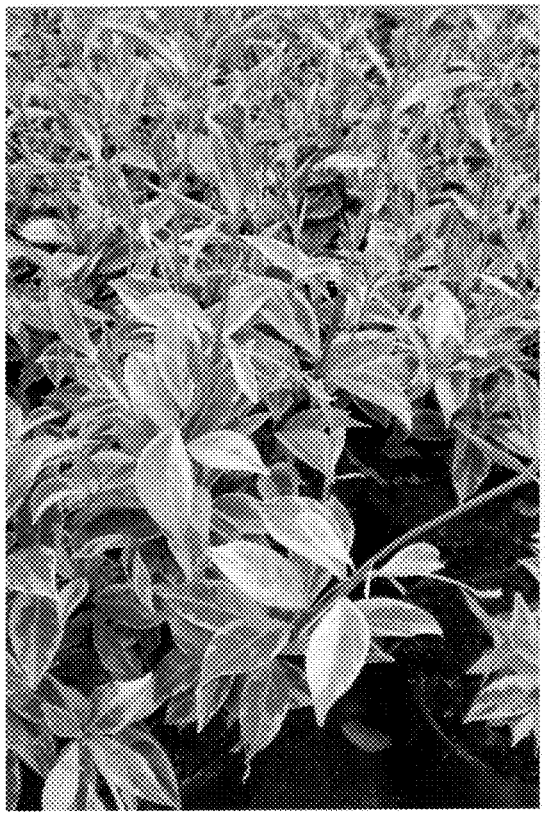
Figure 3:
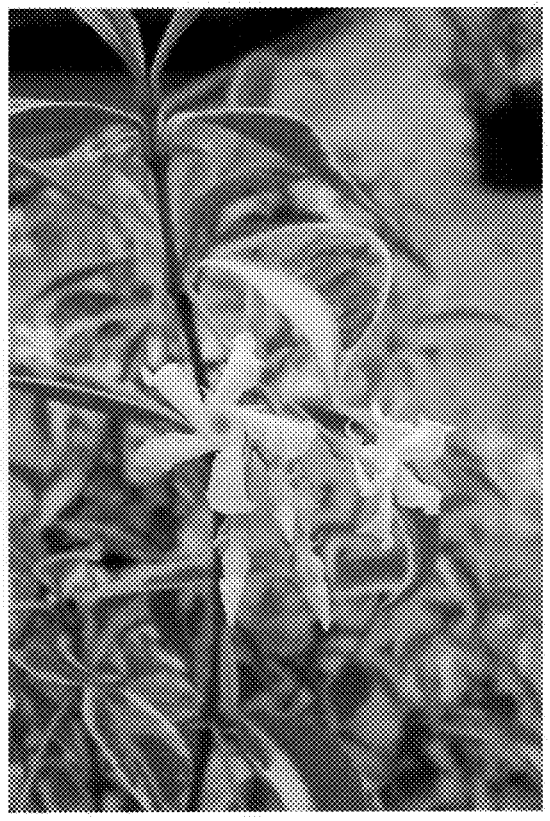
Figure 4:
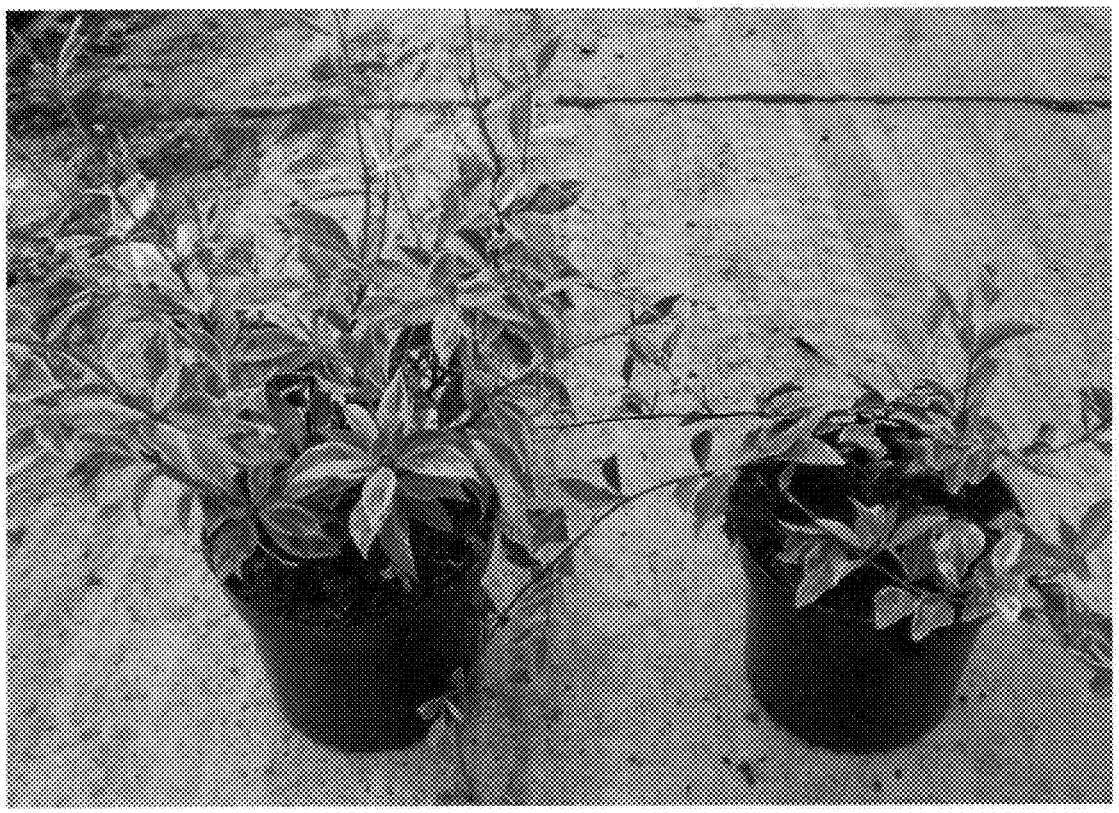

The following is a detailed description of 2 year-old plants of the new star jasmine as grown outdoors in 19 cm containers in Boskoop, The Netherlands. The phenotype of the new cultivar may vary with variations in environmental, climatic, and cultural conditions, as it has not been tested under all possible environmental conditions. The color determination is in accordance with the 2001 RHS Colour Chart of The Royal Horticultural Society, London, England, except where general color terms of ordinary dictionary significance are used.

General description:

*Blooming period.*—Blooms from spring into summer in The Netherlands.

*Plant habit.*—Perennial, deciduous, compact, upright shrub-like vine.

*Height and spread.*—Reaches about 43.5 cm in height and 47.8 cm width in 2 years without support.

*Hardiness.*—At least in U.S.D.A. Zone 8a to 10.

*Diseases resistance.*—No disease problems were observed.

*Root description.*—Fibrous.

Growth and propagation:

*Propagation.*—Softwood stem cuttings.

*Root development.*—Roots develop in about 30 days at 20° C., about 12 months to finish a rooted cutting in a 13 cm container or larger.

*Growth rate.*—Vigorous.

Stem description:

*Shape.*—Round.

*Stem color.*—Young growth; 146A, mature wood N199B to N199C.

*Stem size.*—An average of 12.3 cm in length and 2 mm in width.

*Stem surface.*—Slightly glossy with young stems covered with short adpressed hairs; about 0.5 mm in length and N199C to N199D in color.

*Internode length.*—Average of 3.5 cm.

*Branching.*—About 22 lateral branches are produced on a 2 year-old plant.

*Other stem characteristics.*—Produces a milky fluid when damaged.

Foliage description:

*Leaf shape.*—Narrowly elliptic.

*Leaf division.*—Simple.

*Leaf base.*—Cuneate to attenuate.

*Leaf apex.*—Narrowly acute to apiculate and pointed downwards.

*Leaf fragrance.*—None.

*Leaf venation.*—Pinnate, color on upper surface 145C, color on lower surface 146B.

*Leaf margins.*—Entire.

*Leaf arrangement.*—Opposite.

*Leaf attachment.*—Petiolate.

*Leaf surface.*—Glabrous and smooth on upper and lower surface with upper surface glossy.

*Leaf texture.*—Leathery.

*Leaf size.*—Average of 6.2 cm in length and 2.3 cm in width.

*Leaf quantity.*—Average of 8 per lateral branch.

*Leaf color.*—New growth upper surface; 143A to 144A (slightly darker) with irregular margins of 153D to 6B, new growth lower surface; 146D with irregular margins a color between 153D and 6C, mature leaves upper surface; 137A blotched with 191B to 191D and irregular margins 150D to 157A, mature leaves lower surface; 146C to 146D with narrow margin 150C to 150D.

*Petioles.*—An average of 6 mm n length and 1.5 mm in width, 146C in color, glabrous surface.

*Stipules.*—Not present.

Inflorescence description:

*Inflorescence type.*—Axillary and terminal cymes.

*Inflorescence size.*—About 7.4 cm in depth (including peduncle) and 4.3 cm width.

*Flower buds.*—Oblanceolate in shape, about 1.5 cm in length and 3 mm in width, color is 155C with base 145D.

*Flower fragrance.*—Strong jasmine scent.

*Lastingness of flowers.*—Individual flowers last about 7 days, about 2 flowers open in cyme at a time, self cleaning.

*Flower quantity.*—Average of 6 flowers per cyme, about 16 flowers per lateral stem, 350 flowers per plant (2 years in age).

*Flower type.*—Perfect, rotate.

*Flower aspect.*—Outward to drooping.

*Flower size.*—Average of 2.3 cm in diameter and 1.4 cm in depth.

*Peduncles.*—Average of 5.3 cm in length and 1 mm in diameter, 145C in color, glabrous surface, round in shape, held at about a 90% angle to stem (0% equal to flat on stem).

*Pedicels.*—Average of 1.2 cm in length and 0.8 mm in diameter, 143B in color, glabrous surface, round in shape, terminal cyme flower held on peduncle with lateral flowers held at about a 50% angle to peduncle (0% equals straight up on peduncle).

*Calyx form.*—Rotate with sepals fused at base and curled backwards.

*Sepals.*—5, lanceolate in shape, narrowly acute apex, cuneate base, an average of 7 mm in length and 1 mm in width, entire margin, color of upper and lower surface (immature flowers); 145D, color of upper and lower surface (mature flowers); 157D, glabrous surface.

*Corolla.*—Rotate in form with lower 40% fused into a tube.

*Petals.*—5, un-fused lobes are flabellate in shape and curled lengthwise (involute), upper and lower surface is smooth and very slightly glossy, margin entire and undulate, fused base, rounded to praemorse apex, about 2.0 cm in length and 1.0 cm in width, color of upper surface when opening and fully open; whiter than 155A with top of tube 155A, color of lower surface when opening and fully open; whiter than 155A with tube portion 157B to 157C, non-fading.

Reproductive organs:

*Gynoecium.*—Pistil; 1, about 4.5 mm in length, style; average of 3 mm in length, 145D in color, stigma; club-shaped, 145B to 145C in color, ovary; 143B in color.

*Androcoecium.*—Stamens; 5, anthers; narrow triangular in shape, an average of 3 mm in length, 153D in color, pollen; low in quantity, 4D in color.

It is claimed:

1. A new and distinct cultivar of *Trachelospermum* plant named 'Sunlover,' as herein illustrated and described.

* * * * *